US00PP11886P2

(12) United States Plant Patent
Fruehwirth

(10) Patent No.: US PP11,886 P2
(45) Date of Patent: May 22, 2001

(54) POINSETTIA PLANT NAMED 'ECKABBE'

(75) Inventor: Franz Fruehwirth, Encinitas, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/427,734

(22) Filed: Oct. 27, 1999

(51) Int. Cl.[7] ..... A01H 5/00
(52) U.S. Cl. ..... Plt./307
(58) Field of Search ..... Plt./303, 306, 307

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Poinsettia plant named 'Eckabbe', characterized by its relatively small crimson red bracts that are held horizontally; relatively early flowering; response time about 8 weeks; freely flowering habit; very dark green leaves with red purple petioles; upright plant habit; freely branching habit; and excellent postproduction longevity.

2 Drawing Sheets

BACKGROUND OF THE INVENTION

The present invention relates to a new and distinct cultivar of Poinsettia plant, botanically known as *Euphorbia pulcherrima* Willd., and hereinafter referred to by the name 'Eckabbe'.

The new cultivar is a product of a planned breeding program conducted by the Inventor in Encinitas, Calif. The objective of the program is to create new Poinsettia cultivars having interesting bract and leaf display, color and form; strong and freely branching stems; and good postproduction longevity.

The new cultivar originated from a cross made by the Inventor of the proprietary selection identified as 529, as the female, or seed parent, with the proprietary selection identified as 587, as the male, or pollen parent.

The cultivar 'Eckabbe' was discovered and selected by the Inventor as a flowering plant within the progeny of the stated cross in a controlled environment in Encinitas, Calif. in 1995.

Asexual reproduction of the new Poinsettia by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckabbe'. These characteristics in combination distinguish 'Eckabbe' as a new and distinct cultivar:

1. Relatively small crimson red bracts that are held horizontally.
2. Relatively early flowering; response time about 8 weeks.
3. Freely flowering.
4. Very dark green leaves with red purple petioles.
5. Upright plant habit.
6. Freely branching habit.
7. Excellent postproduction longevity.

In side-by-side comparisons conducted in Encinitas, Calif., plants of the new Poinsettia flower earlier and have more upright bracts than plants of the female parent, the selection 529. Compared to plants of the male parent, the selection 587, plants of the new Poinsettia flower earlier, have darker leaves, and have darker and smaller bracts.

Plants of the new Poinsettia can be compared to plants of the cultivar '490', disclosed in U.S. Plant Pat. No. 7,825. However, in side-by-side comparisons conducted in Encinitas, Calif., plants of the new Poinsettia differed from plants of '490' in the following characteristics:

1. Plants of the new Poinsettia are slightly taller than plants of '490'.
2. Plants of the new Poinsettia have smaller leaves than plants of '490'.
3. Flower bracts of the new Poinsettia are slightly smaller and brighter red than flower bracts of '490'.
4. Plants of the new Poinsettia have more cyathia and larger cyathia clusters than plants of the cultivar '490'.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type.

The photograph at the top of the first sheet comprises a side perspective view of a typical plant of 'Eckabbe'.

The photograph at the bottom of the first sheet comprises a top perspective view of a typical plant of 'Eckabbe'.

The photograph on the second sheet is a close-up view of typical bracts and leaves of '490' (left) and 'Eckabbe' (right). Bract and foliage colors in the photographs may differ from actual colors due to light reflectance.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a glass-covered greenhouse with day temperatures ranging from 21 to 27° C., night temperatures ranging from 18 to 20° C., and light levels about 4,000 foot-candles. Plants were grown in 16-cm pots, pinched one time, and flowered under naturaly lengthening nyctoperiods during the fall/early winter. Plants were about 16 weeks old after planting from an unrooted cutting.

In the following description, color references are made to The Royal Horticultural Society Colour Chart except where general terms of ordinary dictionary significance are used.

Botanical classification: *Euphorbia pulcherrima* Willd. 'Eckabbe'.

Parentage:

*Female parent.*—Proprietary selection of *Euphorbia pulcherrima* Willd. identified as 529.

*Male parent.*—Proprietary selection of *Euphorbia pulcherrima* Willd. identified as 587.

Propagation:

*Type cutting.*—Terminal cuttings.

*Time to initiate roots.*—Summer: About 7 days at 24° C. Winter: About 10 days at 22° C.

*Time to develop roots.*—Summer: About 26 days at 24° C. Winter: About 26 days at 22° C.

*Root description.*—Freely branching, becoming fibrous with development.

Plant description:

*Plant form.*—Inverted triangle.

*Growth habit.*—Upright. Freely branching. Branching is enhanced by removing the shoot apex. Moderately vigorous.

*Plant height.*—About 30 cm.

*Crop time.*—From unrooted cuttings to a flowering plant in a 16-cm container, about 16 weeks are required.

*Stem description.*—Number of lateral branches: About seven lateral branches are formed after removal of the terminal apex. Lateral branch length: About 20 cm. Internode length: About 1.75 cm. Stem color: 146A to 146B.

*Foliage description.*—Quantity of leaves per lateral branch: About 8. Length: About 11 cm. Width: About 6.5 cm. Shape: Ovate. Apex: Acuminate. Base: Acute. Margin: Entire. Texture: Smooth, dull; very sparse pubescence on lower surface. Color: Young foliage, upper surface: Darker than 147A. Young foliage, lower surface: 147A. Mature foliage, upper surface: Darker than 147A. Mature foliage, lower surface: 147A. Venation, upper surface: 147B. Venation, lower surface: 147C to 147D. Petiole: Length: About 4.5 cm. Diameter: About 2 mm. Color: 59A.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long nyctoperiod conditions. Response time is about 8 weeks.

*Quantity of inflorescences.*—One per lateral branch, usually about seven per plant.

*Inflorescence size.*—Diameter: About 28 cm. Height (depth): About 4.5 cm.

*Flower bracts.*—Quantity of flower bracts per inflorescence: Usually about 12 primary bracts and about 8 smaller secondary bracts per inflorescence. Length, largest bracts: About 14 cm. Width, largest bracts: About 8 cm. Shape: Ovate. Apex: Acuminate. Base: Acute. Margin: Entire. Texture: Smooth. Aspect: Held mostly horizontal. Color: Developing, upper surface: Brighter than 46A. Developing, lower surface: 46B. Mature, upper surface: More crimson than 46B. Mature, lower surface: 45B.

*Cyathia.*—Quantity: Usually about 14 per corymb. Diameter of cyathia cluster: About 3 by 4 cm. Length: About 1 cm. Width: About 6 mm. Color: Immature: 144B. Mature: 144B to 144C. Peduncle: Length: About 6 mm. Aspect: Strong, erect. Color: 144B. Stamens: Stamen number: Five with numerous stamenoids per cyathium. Anther length: About 1 mm. Anther shape: Oval. Anther color: 45A. Amount of pollen: Scarce to moderate. Pollen color: 7A. Pistils: None. Nectaries: Nectary quantity: One per cyathium. Nectary color: 14A.

Disease resistance: Plants of the new Poinsettia have been observed to be resistant to Botrytis.

Postproduction longevity: Excellent; generally plants maintain good substance and bract color for about eight weeks under interior conditions.

It is claimed:

1. A new and distinct cultivar of Poinsettia plant named 'Eckabbe', as illustrated and described.

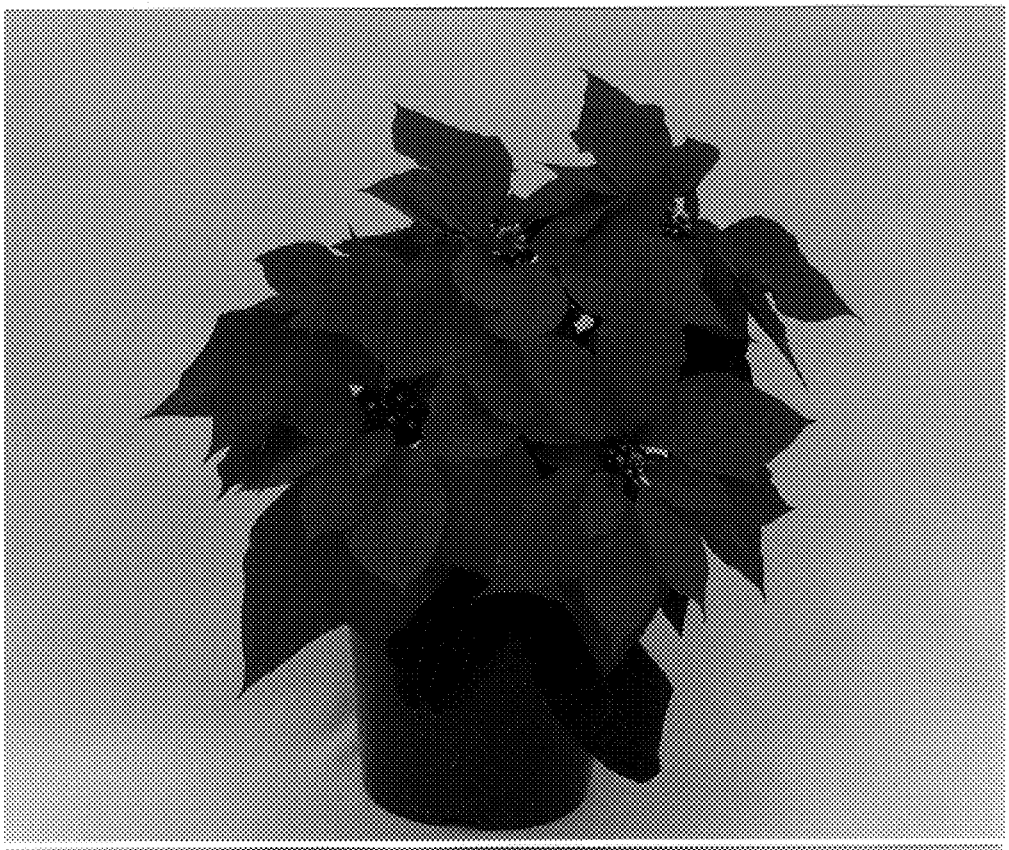
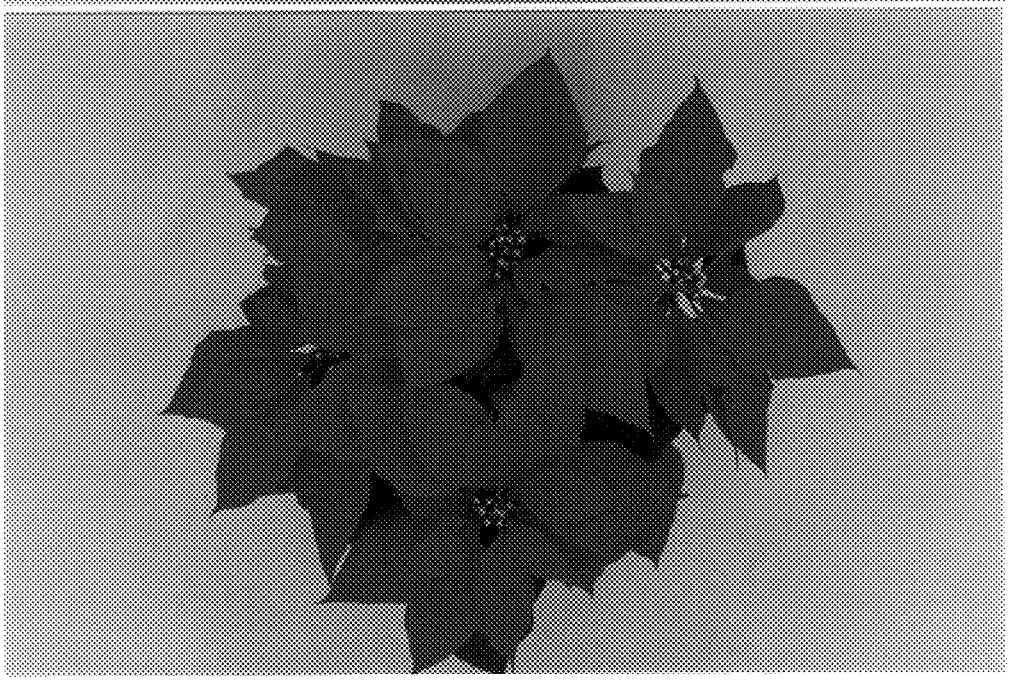

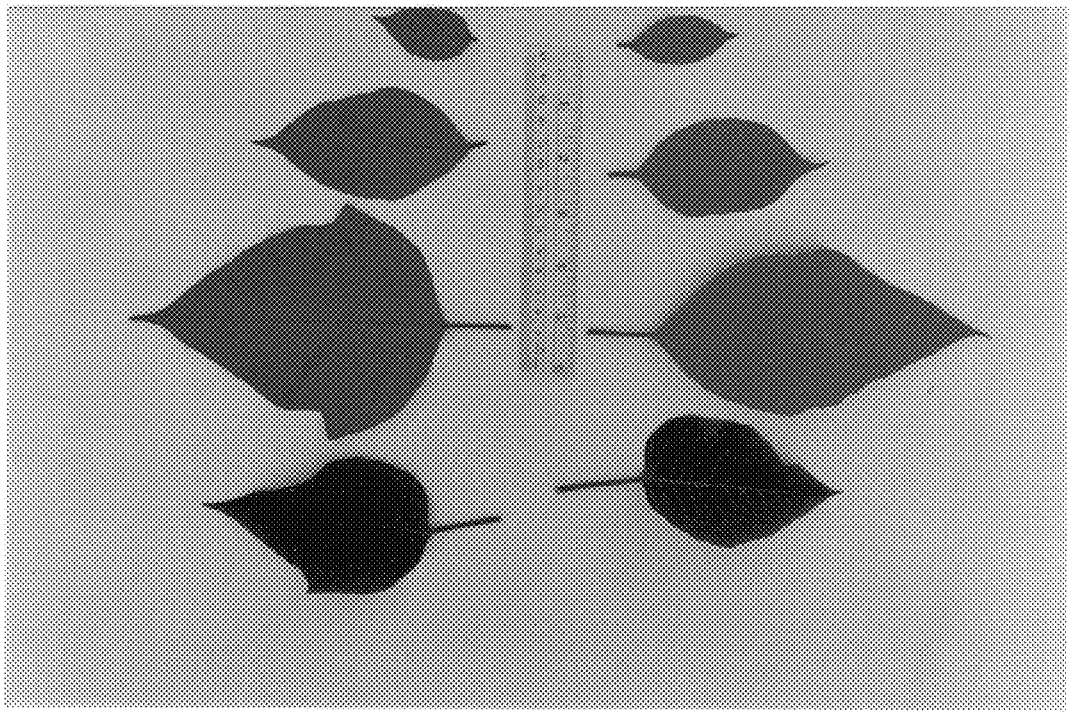

* * * * *